United States Patent [19]
Crambes

[11] Patent Number: 4,565,088
[45] Date of Patent: Jan. 21, 1986

[54] PROCESS AND APPARATUS FOR THE DETECTION OF CHANGES OF COMPOSITION IN A MEDIUM WITH THE AID OF ULTRASOUND

[75] Inventor: Michel Crambes, Villette de Vienne, France

[73] Assignee: Elf France, France

[21] Appl. No.: 574,971

[22] Filed: Jan. 30, 1984

[30] Foreign Application Priority Data

Jan. 31, 1983 [FR] France .................. 83 01427

[51] Int. Cl.⁴ ............................................. G01N 29/02
[52] U.S. Cl. .............................. 73/61.1 R; 73/290 V
[58] Field of Search .................. 73/61.1 R, 290 V; 340/624

[56] References Cited

U.S. PATENT DOCUMENTS 3,693,445  9/1972  Johnson .................. 73/290 V
4,403,508  9/1983  Langlois .................. 73/290 V X
4,424,701  1/1984  Mair ........................ 73/290 V X

FOREIGN PATENT DOCUMENTS 1123939   8/1968  United Kingdom ............ 73/290 V
1131299  10/1968  United Kingdom ............ 340/624
1399977   7/1975  United Kingdom ............ 73/290 V

*Primary Examiner*—Charles Hart
*Attorney, Agent, or Firm*—Ostrolenk, Faber, Gerb & Soffen

[57] ABSTRACT

Process and apparatus for detecting and locating a change of composition in a medium, which consists in determining the speed of transmission of an ultrasonic wave through a layer or column of the medium; this determination is effected at a plurality of locations or levels and those of the locations or levels are noted which correspond to changes in the speed of transmission of the wave.

11 Claims, 1 Drawing Figure

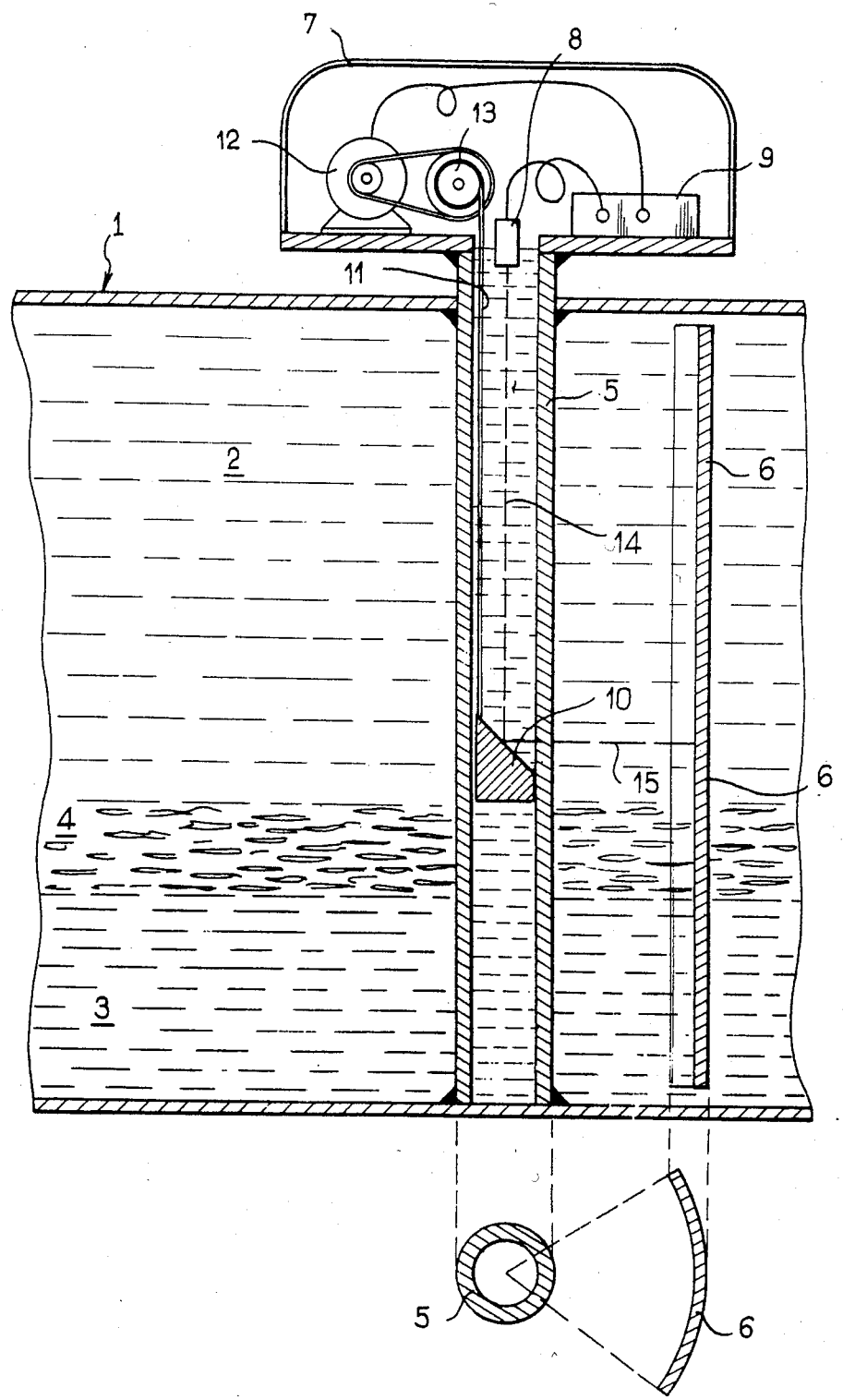

PROCESS AND APPARATUS FOR THE DETECTION OF CHANGES OF COMPOSITION IN A MEDIUM WITH THE AID OF ULTRASOUND

The present invention relates to a process utilizing ultrasonic waves for locating changes of composition which can occur in a solid and/or fluid medium. It also renders possible determination of the thickness of the layer where the composition differs from the remainder of the medium. The invention also concerns an apparatus for carrying out this process. In particular, it relates to a process and an apparatus for the detection and, if required, the measurement of a layer of a water-hydrocarbon emulsion in a hydrocarbon.

It often happens in industry, in the course of manufacture or during storage of a product, that one or more layers of different composition form at various levels and—for technical reasons—it is necessary to know where they are located within the vessel, receptacle or tank which contains the product in question. In particular, this knowledge permits reliable separation of only the desired layer. For example, such a situation occurs in the precipitation in water of metal pigments or hydroxides, such as magnesia, alumina, ferric hydrate, etc., or also phosphates or other insoluble slowly separating compounds; it is very useful to know at a given time where the plane of separation between the supernatant liquid and the suspension of the precipitate is located. The question is particularly important when the fluid is treated in a closed or sealed receptacle or apparatus, which cannot include transparent areas, and particularly if it is at an elevated temperature and—possibly—under pressure. Such a case occurs in the petroleum industry, notably during the desalination of crude oil. It is known that this operation is effected in steel cylinders of large dimensions, having thermally-insulated walls; the oil is under a pressure of several bars and its temperature can attain 150° C. The water present, of the order of 10%, settles to the bottom, receiving droplets of salinated water emulsified in the crude oil; the resolution of the emulsion is generally produced by an alternating electrical field, maintained between two grids disposed longitudinally in the cylinder; however, this is not complete and a layer of emulsion often remains at a level between the separated water and hydrocarbon. It is thus important to know the level, in order not to withdraw the emulsion together with the water being rejected or with the oil being recovered. Because of the abovementioned construction of the desalinator, it is not possible to ascertain from outside at which level and to where the pre-existing layer of the emulsion extends. The standard methods, using a mechanical system for measuring levels, or optical procedures, including those employing lasers, are thus not suitable. Measurement of the dielectric constant, which can be done in a closed apparatus, always presents problems, in dealing with just detectable variations in the distribution of salinated water in the oil, and is rarely reliable. It is thus highly desirable to find a process which can serve in the cases mentioned above.

The present invention fulfils this desire and allows the detection with precision and reliability of any layer of different composition within a given medium. It is applicable both to open and closed receptacles, having walls which are good or bad conductors of sound.

The novel process according to the invention is based upon determination of the speed of transmission of an ultrasonic wave through a column or layer of the medium concerned, at a plurality of locations or levels. As the speed of sound varies with the composition of the medium, a detectable variation in this speed indicates the location where the composition has changed.

It is known that the speed of propagation of ultrasound in water is distinctly higher than in lubricating oil, which allows—by quantitative measurement—metering of the proportion of oil in an aqueous lubricant emulsion. Thus, it can be seen, for example, in British Pat. No. 1437851 that a wave having a frequency of 1 MHz travels at 50° C. at a speed of 1540 m/s in water, as against 1290 m/s in the lubricant; the difference increases with temperature to become respectively 1550 as against 1150 at about 70° C. According to the cited patent, this circumstance is applied to measurement of the oil in an aqueous lubricant emulsion, namely a static operation in which emission of the ultrasonic wave and measurement of the ultrasonic speed by reception of the echo always take place at the same location.

In contrast, the present invention applies measurement of the speed of propagation of ultrasound in a new and kinetic manner, over the length of a vertical layer or column of the medium tested, in order to monitor it and detect the location where a change in the composition begins, as revealed by a change in the ultrasonic speed. Thus the invention allows determination of the concentration profile of a constituent of the medium along a measurement axis.

In the following part of the present description, the invention is described as applied to liquid media, but it is to be understood that it can be utilized in different cases in solid, liquid and/or gaseous media.

According to the invention, an ultrasonic wave is transmitted at a plurality of levels in the liquid in question, at such an angle relative to a deflector or screen immersed in the liquid that the echo can be received. With the aid of an electronic device, known per se, using the time elapsed between emission and return of the echo, for a given distance between the emitter and the screen, the ultrasonic speed in the liquid at the different levels can be determined. It is thus simple to indicate and/or register by electronic means the speeds thus measured, either as such or their variations, so as to determine the levels where the changes of composition are located.

In this way, it is possible to monitor efficiently the separation of different precipitates or liquids, the existence of a layer of emulsion in hydrocarbons etc.

The process of the invention can be carried out continuously, in principle, that is with a series of ultrasound emitters and receptors functioning at the same time, at different levels of the receptacle containing the liquid being tested; responses are thus continuously obtained which characterize the different levels. However, from the standpoint of the apparatus required, this process is complicated, because it requires a large number of ultrasonic probes and electronic equipment.

A more economical embodiment of the new process consists in vertically displacing an ultrasound emitter-receptor system along the liquid column which is being monitored and making it operate at a plurality of positions.

An even more practical solution lies in the use of a fixed ultrasound emitter-receptor with its electronic system, which directs a wave of the desired frequency toward a mirror which is displaced along the liquid column being surveyed.

While vertical investigation of a fluid mass corresponds to the most frequent kind of industrial operation, the process of the invention can also apply to investigation in a horizontal or an inclined direction, where required.

The detection according to the invention can take place with the aid of ultrasonic waves of very varied frequencies, which are either monochromatic or polychromatic. However, because ultrasounds of relatively low frequency exert a dispersing action on materials which they traverse, it is preferable in carrying out the invention to utilize frequencies higher than 50 kHz or, better still, higher than 200 kHz. On the other hand, as ultrasounds of very high frequencies are strongly absorbed, that is they are attenuated in the medium traversed, it is preferable according to the invention to choose frequencies in the range from 200 kHz to 5 MHz or, better still, from 500 kHz to 3 MHz. In the case of emulsifiable liquids, for example hydrocarbons with water, particularly favourable results are obtained with frequencies of 1.2 to 2.7 MHz.

The apparatus for carrying out the most practical embodiments of the process according to the invention comprises a probe, namely an ultrasound emitter and receptor, as well as an electronic system for treating the electrical responses of the receptor; it is characterized by means for displacing, according to a predetermined rhythm, either the emitter-receptor or a mirror for reflection of the waves received from the emitter, along the path over which the measurements are to be effected.

Depending upon the nature of the walls of the receptacle in which variations of the composition at certain levels are to be observed, the probe can be placed against one of these walls or may be located in a tube immersed in the contents of the receptacle. The first of these arrangements is the simpler and is appropriate when the walls are of a material which is a good conductor of sound, particularly a bare metal. Thus, for example, as the speed of ultrasound transversely in steel is about four times higher than its speed in water, the probe can be placed against the external steel wall of the apparatus; it can be displaced along this wall in order to locate the level where the composition changes. However, a reflective screen must then be installed inside the receptacle to direct the echo towards the receptor.

If the walls of the receptacle are of a material which is a poor conductor of sound, for example wood, or metal covered with thermal insulation, or if the wall has no plane surface in the axis of measurement, the probe must be put inside the receptacle. It is preferably located in a tube having a metal wall, filled with a liquid which is a good transmitter of ultrasound, for example water, glycerol, glycerol-containing water, silicone oil or others. In this case, the reflector screen should be concentric with the metal-walled tube.

As ultrasonic probes are well known in the art, they will not be described here; mention will merely be made that their transducer, generating the ultrasonic wave under the action of an electrical potential, is a piezoelectric or ferroelectric material, in particular quartz or Pb titanate-zirconate.

As regards the reflector screen, it is preferably of a material having an acoustic impedance which ensures good reflection of ultrasounds in the medium tested, while being compatible with this medium. In the case of a water-crude oil emulsion, a stainless steel screen can be used, for example. This screen is preferably semicircular in section and is coaxial with the tube which contains the probe and/or the mirror. It is suitable to maintain the probe and/or the mirror so as to prevent any rotation around the axis of displacement of these components. It is desirable that neither the screen nor the tube to have too large a diameter; the preferred exterior diameters of the tube are from 30 to 100 mm and the distance between the tube and the screen is preferably 100 to 400 mm or, even better, 150 to 350 mm.

By way of non-limitative example, the single FIGURE attached shows an apparatus according to the invention, in which the ultrasonic probe is fixed, while a mirror is displaceable in a tube along a vertical column of the liquid to be tested.

In the drawing, 1 represents diagrammatically and partially a metal cylinder containing a system of two liquids, 2 and 3, between which a phase of changed composition forms at 4. This is the case particularly inside a crude oil desalinator in which an emulsion of water in the oil occurs at 4.

Between the upper and lower walls of the cylinder 1, a steel tube 5 having an external diameter of 80 mm is fixed, with a short upward extension. On the other hand, a stainless steel screen 6, concentric with the tube 5 and describing about a quarter of a circle, is placed at a distance of 20 cm from the latter.

In the upper end of the tube 5, an ultrasound emitter-receptor 8 is located. This probe comprises a piezoelectric crystal and has the construction known per se; it is connected to an electronic system 9 comprising an HF generator, a microprocessor and a servo-motor 12. The motor, the electronic system and a winch 13 are mounted in a casing 7 at the upper part of the tube 5.

The tube 5 is filled with silicone oil, in which is immersed a stainless steel mirror 10, arranged at an angle of 45° with respect to the axis of the tube. In accordance with the invention, the mirror 10 is attached to a cable 11 connected to the winch 13. By switching on the motor 12, the winch 13 is operated and it raises or lowers the mirror 10, while monitoring the whole of the height of the liquid layer in the cylinder 1. During this time, the emitter 8, also immersed in the silicone oil, emits ultrasonic waves along the axis of the tube 5, as shown by the broken line 14.

As the upper face of the mirror makes an angle of 45° to the axis of the tube, the wave reflected on it, as shown at 15, is perpendicular to the reflector screen 6. The effect of the reflection is such that the echo is received in the receptor 8 along the line 14. The speed of the ultrasound over the path 15 is calculated, in known manner, by the electronic system 9. Information is thus rapidly obtained about a change in composition in the region 4; when the mirror 10 reaches this level, the sonic speed indicated is clearly different from that read off at the level of the liquid 2. Thus, with ultrasounds of 2 MHz, the speed of propagation is 730 m/s in crude oil at 150° C., while the speed rises to 835 m/s at the same temperature, when 10% of water is dispersed in the crude oil. For a stronger emulsion, in particular 30%, the speed attains 1025 m/s. It is thus a simple matter to locate the level where the emulsion of the water in the oil commences. Operation occurs in a similar fashion when the change in composition concerns a precipitate or another separate liquid phase.

I claim:

1. Process for detecting and locating a change of composition in a medium by means of ultrasound which comprises:

positioning a medium tight tube in the medium, the tube having a mirror which reflects ultrasonic waves along the longitudinal axis of the tube perpendicularly to said axis, said mirror being displaceable to a plurality of points along said axis;

positioning a reflector screen which surrounds a portion of the tube to reflect ultrasonic waves perpendicular to said axis of the tube back to the mirror in said medium a distance of 100 to 400 mm from the tube;

transmitting ultrasonic waves along said axis;

displacing said mirror in said tube to a plurality of said points; and determining the ultrasonic speed of the medium between the tube and the reflector screen at said plurality of points along said axis.

2. Process according to claim 1 wherein the frequency of the ultrasonic waves is in the range from 200 kHz to 5 MHz.

3. Process according to claim 2 wherein the frequency is 500 kHz to 3 MHz.

4. Process according to claim 3 wherein the frequency is 1.2 to 2.7 MHz.

5. Process according to claim 4 wherein said reflector screen is concentric with said tube and subscribes about a quarter of a circle.

6. Process according to claim 5 wherein said medium comprises a hydrocarbon and water whereby the region of water-in-hydrocarbon dispersion is detected and located.

7. Apparatus for the detection of a change in the composition of a medium in a vessel which comprises in combination, a medium tight tube extending into said medium and secured to said vessel;

an ultrasound emitter-receptor disposed so as to transmit ultrasonic waves along the longitudinal axis of said tube;

electronic means connected to said emitter-receptor for determining the speed of ultrasonic waves in said medium;

a mirror in said tube displaceable to a plurality of points along said axis and having a reflecting surface oriented at 45° with respect to said axis;

means to displace said mirror to said plurality of positions along said axis, and a reflector screen disposed in said medium to reflect ultrasonic waves back to said mirror, said reflector screen surrounding a portion of the tube surface at a distance of 100 to 400 mm therefrom.

8. Apparatus according to claim 7 wherein said tube has a diameter of 30 to 100 mm.

9. Apparatus according to claim 8 wherein said reflector screen is coaxial with said tube and is at a distance of 150–300 mm therefrom.

10. Apparatus according to claim 9 wherein said reflector screen subscribes a quarter of a circle.

11. Apparatus according to claim 10 wherein said tube is filled with a silicone oil.

* * * * *